| United States Patent [19] | [11] Patent Number: 5,053,522 |
| --- | --- |
| Muller | [45] Date of Patent: Oct. 1, 1991 |

[54] PROCESS FOR THE PREPARATION OF LACTIDE

[75] Inventor: Manfred Muller, Bickenbach, Fed. Rep. of Germany

[73] Assignee: Boehringer Ingelheim KG, Ingelheim am Rhein, Fed. Rep. of Germany

[21] Appl. No.: 347,856

[22] Filed: May 5, 1989

Related U.S. Application Data

[63] Continuation of Ser. No. 99,561, Sep. 22, 1987, abandoned.

[30] Foreign Application Priority Data

Mar. 19, 1987 [DE] Fed. Rep. of Germany ....... 3708915

[51] Int. Cl.$^5$ .......................................... C07D 319/12
[52] U.S. Cl. ..................................... 549/274; 502/151
[58] Field of Search .......................................... 549/274

[56] References Cited

U.S. PATENT DOCUMENTS

| 1,095,205 | 5/1914 | Gruter | 549/274 |
| 4,157,330 | 6/1979 | Reuter et al. | 549/267 |
| 4,165,321 | 8/1979 | Harris et al. | 549/267 |
| 4,393,223 | 7/1983 | Harris | 549/549 |
| 4,789,726 | 12/1988 | Hutchinson | 528/361 |

FOREIGN PATENT DOCUMENTS 1108720 4/1968 United Kingdom ................ 549/274

*Primary Examiner*—C. Warren Ivy
*Assistant Examiner*—Amelia A. Owens
*Attorney, Agent, or Firm*—D. E. Frankhouser; A. R. Stempel; M-E. M. Timbers

[57] ABSTRACT

The invention relates to a process for the preparation of lactide, in particular of optically pure L(−)- or D(+)-lactide, on an industrial scale.

3 Claims, No Drawings

PROCESS FOR THE PREPARATION OF LACTIDE

This is a continuation of application Ser. No. 099,561, filed Sept. 22, 1987.

The invention relates to a process for the preparation of lactide, in particular of optically pure L(—)- or D(+)- lactide on an industrial scale.

The preparation of lactide has been known for a long time from a large number of patent specifications and Offenlegungsschriften.

Thus, German Patent Specification 267826 claims a process for the preparation of lactide, wherein lactic acid is slowly heated to a temperature of 200° C. and the lactide thus formed is distilled off, advantageously in vacuo.

German Patent Specification 1234703 discloses the preparation of optically active L(—)-lactide from an aqueous solution of L(+)-lactic acid in the presence of a titanium tetraalkoxide. German Auslegeschrift 1083275 describes a preparation process, wherein the depolymerisation can be carried out in the presence of metals or compounds thereof from groups IV, V or VIII of the Periodic Table. Zinc oxide, tin oxide and antimony oxide are mentioned in the Examples as catalysts. Moreover, the use of lead(II) stearate as a depolymerisation catalyst is known from German Offenlegungsschrift 1543958.

In their Examples, the above mentioned publications only describe reactions on the laboratory scale, that is to say up to about 1 kg. It has been found in practice, however, that the direct scale-up to industrial scale, even of successful laboratory experiments, of the preparation of lactide, especially optically pure lactide, raises problems where the optical purity and the chemical yield inter alia are to be regarded as criteria. The yields, disclosed in German Auslegeschrift 1083275, of the processes described prove not to be reproducible even in laboratory experiments.

Whereas J. Klein in Macromol. Chem. 30, 35 (1959), reports that the depolymerisation of polylactide in the presence of zinc dust proceeds in a 90% yield, these high yields cannot be achieved in a production process carried out on the industrial scale. A large-scale process, such as is practiced industrially, uses L(+)-lactic acid as the starting material, which is thermally converted into L(—)-polylactic acid and then depolymerised to L(—)-lactide in the presence of a zinc powder catalyst. According to this process, about 168 kg of optically active L(—)-lactide of satisfactory quality can be obtained in one batch, starting from about 440 kg of L(+)-lactic acid; this corresponds to a yield of about 50 to 55% (relative to L(+)-lactic acid). In this process it is necessary to clean the reaction vessel after each batch, for which generally half-concentrated sodium hydroxide solution is used.

Apart from the fact that only yields between 50 and 55% can be achieved in the industrial process described, this process proved to be very costly, since the reaction apparatus, both during the dehydration of the L(+)-lactic acid and during the cleaning phase, cannot be utilised for the production of L(—)-lactide.

Attempts to convert this batchwise-operating process to a continuous or semi-continuous process surprisingly led to a deterioration in the overall yield and to a reduction in the optical purity of the L(—)-lactide.

A further disadvantage of the preparation processes known from the state of the art is that, to obtain high optical purity in the case of optically active lactides, the depolymerisation must be followed by several purification steps.

It is the object of the present invention to provide a process for the preparation of lactide, in particular optically pure L(—)- or D(+)-lactide, on an industrial scale, which allows an improved utilization of the raw material employed.

It is a further object of the present invention to propose a process for the preparation of optically active lactide, which shows both a higher chemical yield and a higher optical purity.

According to the invention, this object is achieved when polylactic acid is heated under a reduced pressure to 130° to 230° C. in the presence of 0.05 to 1.0% by weight of tin dust, a tin halide or an organic tin compound derived from a carboxylic acid having up to 20 carbon atoms, the lactide formed is distilled off and additional polylactic acid is fed in continuously or batchwise.

Tin compounds particularly suitable as catalysts are compounds of the general structure

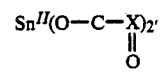

wherein X is a branched or unbranched alkyl, hydroxyalkyl or alkenyl radical having up to 19 carbon atoms or a naphthyl radical, or compounds of the general structure

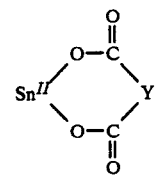

wherein Y is a branched or unbranched alkyl, hydroxyalkyl or alkenyl radical having up to 18 carbon atoms or a phenyl radical.

Examples of alkyl groups suitable for X and Y are the methyl, ethyl, n- or iso-propyl, n-, sec.- or tert.-butyl, pentyl, hexyl, heptyl or octyl radicals which, if appropriate, can contain one or more hydroxyl groups. Corresponding alkenyl radicals contain one or more double bonds. If a tin halide such as, for example, $SnCl_2$ or $SnBr_2$ is used as the catalyst, tin lactate is formed with elimination of the corresponding acid.

The preferred catalysts are tin lactate, tin tartrate, tin oxalate, tin dicaprylate, tin dilaurate, tin dipalmitate, tin distearate, tin dioleate (derivative of oleic acid), tin-naphthoate or tin-naphthoate. Tin dioctoate, better described as tin-di-(2-ethylhexanoate), or tin dust are particularly preferred.

The optically active lactides, L(—)-lactide and D(+)-lactide, are prepared by analogous processes, starting from the corresponding L(—)-polylactic acids and D(+)-polylactic acids respectively.

The polylactic acid employed in the process can be prepared in a separate reaction step according to known processes by dehydration of lactic acid.

In the case of optically active polylactic acids, the starting material is of course prepared from the corresponding optically active lactic acids (L(+)-lactic acid L(−)-polylactic acid; D(−)-lactic acid D(+)-polylactic acid).

In a special embodiment of the process according to the invention, lactic acid is employed in place of polylactic acid. In a first reaction step, the lactic acid is dehydrated in the presence of the catalyst under reduced pressure under rising temperature. In general, dehydration is carried out under pressures of about 0.01 to 0.05 bar, the temperatures in the reactor rising to about 150° to 170° C. When an average molecular weight of the polylactic acid thus formed of about 400 to 2000, preferably 600–800, has been reached, lactide is distilled off continuously and additional polylactic acid is then fed in continuously or batchwise.

In a further embodiment, additional lactic acid can also be fed into the continuous process in place of polylactic acid.

The process for the preparation of L(−)-lactide is described in more detail below, but this description is equally applicable to the preparation of D(+)-lactide, D,L-lactide and meso-lactide by the use of the corresponding polylactic acids or lactic acids.

When starting the reactor, L(−)-polylactic acid is introduced first, and 0.05 to 1.0% by weight, preferably 0.1 to 0.8% by weight, of tin dust, tin halide or the organo-tin compound is added. The reactor is then heated under reduced pressure to 130° to 230° C., preferably 180° to 200° C., the L(−)-lactide formed being distilled off. The optimum temperature range depends on the vacuum applied and can be determined by simple trials. The lowest possible distillation temperature has a favourable effect on the purity of the distillate. After a certain quantity of product has distilled off, additional L(−)-polylactic acid is fed in, advantageously in the molten form. It can be fed in batchwise (in portions) or also in a continuous manner, for example by dropwise addition. It is quite possible for the quantity additionally fed to be greater than the original quantity employed at the start of the reaction.

In the case where the additional L(−)-polylactic acid is fed in batchwise, the residual volume of the reactor contents are not critical within a wide range with respect to the quality of the product, but it is advantageous to top up after a conversion of about 50 to 90%. It cannot be excluded that excessive lowering of the reactor contents leads to a deterioration in the product. In the case where the process is run continuously, the feed is advantageously arranged such that the volume of the reactor contents is kept constant as far as possible.

If L(+)-lactic acid is fed directly to the reactor in place of L(−)-polylactic acid, before the depolymerisation to give lactide a dehydration of the L(+)-lactic acid to L(−)-polylactic acid up to a mean molecular weight of about 400 to 2000, preferably 500 to 800, takes place in the presence of the organo-tin compound or tin dust as the catalyst. The dehydration is carried out preferably under about 0.03 bar at a temperature rising to about 170° C. After the desired molecular weight has been reached, the batch is further processed as described above.

As already stated, it is possible, in a further process variant, to feed additional L(+)-lactic acid in place of L(−)-polylactic acid, in which case water is then again first distilled off from the reaction mixture until the desired molecular weight of the polylactic acid is obtained. The process then continues as described above.

The use or additional feeding of L(+)-lactic acid in place of L(−)-polylactic acid does not have any disadvantages whatsoever, as compared with the variants described above, with respect to the chemical and optical purities. An advantage is that the reaction time for the dehydration of the lactic acid is shortened by about 50%. The molecular weight of the polylactic acid formed is determined by titration of the end groups.

The L(−)-lactide which has been distilled off is worked up by known processes, for example by recrystallisation from an alcohol having 1 to 6, preferably 1–3, carbon atoms, particularly preferably isopropanol, or by dissolution and subsequent precipitation in a non-solvent.

Using the process according to the invention, optically pure L(−)-lactide is obtained up to 80% yield, relative to the feed of L(+)-lactic acid, after working-up including recrystallisation.

The advantages of the process according to the invention are a high yield in a preparation process carried out on an industrial scale, coupled with high optical purity, and a better utilisation of the actual depolymerisation reactor, so that a high throughput (measured in kg/h) can be achieved even with relatively small units.

Whereas a noticeable deterioration in quality of the L(−)-lactide distilled off was observed towards the end of the reaction in the conventional process using zinc dust, the process according to the invention gives a constant high quality even after repeated additional feeding of L(−)-polylactic acid or L(+)-lactic acid; the same also applies to the other lactides.

The process according to the invention allows the preparation of optically active lactides, in particular of L(−)-lactide of an optical purity of >99% ee, when the distillation is followed by a single purification operation such as, for example, recrystallization. Preferably, the recrystallization is from isopropanol.

The Examples which follow explain the invention, but without restricting it.

COMPARATIVE EXAMPLE

Conventional process using zinc as the catalyst 2.2 kg of zinc dust are added to 440 kg of L(+)-lactic acid (90% pure), and the mixture is dehydrated at up to about 180° C. bottom temperature under about 0.035 bar. The L(−)-lactide formed is then distilled off at up to about 230°60 C. under about 0.01 bar. About 263 kg of L(−)-lactide are obtained as the distillate. The residue of about 10–20 kg is removed by means of about 150 kg of dilute sodium hydroxide solution. The distallate obtained is added to 263 kg of isopropanol, which gives 195 kg of L(−)-lactide as crude crystals. Recrystallization from isopropanol with addition of active charcoal gives 168 kg of L(−)-lactide, =53% relative to L(+)-lactic acid, having a melting point of 96°-98° C. and $[\alpha]_D^{25} > -287°$.

EXAMPLE 1

1 kg of tin dust is added to 232 kg of L(−)-polylactic acid of an average molecular weight of 610, and the mixture is heated to 194° C. -198° C. under a vacuum of 25-13 Torr. At the same time, L(−)-lactide distills off. After a distillate quantity of 190 kg of L(−)-lactide has been obtained, an additional 220 kg of L(−)-polylactic acid are fed in and distilled under the conditions given above.

This procedure is repeated several times:

| Distillate quantity: | 188 kg | Additional feed: | 86 kg |
|---|---|---|---|
| | 154 kg | | 226 kg |
| | 178 kg | | 405 kg |
| | 355 kg | | 393 kg |
| | 370 kg | | 396 kg |
| | 363 kg | | 409 kg |
| | 378 kg | | 429 kg |
| | 398 kg | | 401 kg |
| | 374 kg | | |

Residue: 20 kg
Throughput: L(−)-polylactic acid: about 44 kg h
The distillate is worked up as described in the comparison Example.
Total yield: 2110 kg of L(−)-lactide=64.8% of theory relative to L(+)-lactic acid employed
Optical purity: >99% ee L(−)-lactide
Specification: 96°-98° C. $[\alpha]_D^{25} > -289.6°$ (toluene)
In place of Sn dust or Sn powder, the reaction can also be carried out with 3.4 kg of tin dioctoate. The throughput is then increased to 75 kg h.

EXAMPLE 2

3.4 g of tin dioctoate are added to 798 g of L(+)-lactic acid of 90% purity (Lactol 90), and the mixture is converted to polylactic acid at a bottom temperature of about 170° C. After 4.0 hours, an average molecular weight of 748 has been reached. 531 g of L(−)-lactide are then distilled off under about 0.01 bar and up to about 200°60 C. bottom temperature within 1 hour and 35 minutes. Additional Lactol 90 is fed to the distillation bottoms, and this is again converted to L(−)-lactide under the conditions given above. This procedure is repeated several times:

| Additional Lactol 90 fed in | PLA formation time | MW | L(−)-lactide distillation time | Distillate quantity g |
|---|---|---|---|---|
| 800 | 3 h 50 min | 724 | 2 h 30 min | 561 |
| 795 | 4 h | 687 | 2 h 25 min | 529 |
| 795 | 3 h 40 min | 778 | 2 h 10 min | 542 |
| 827 | 9 h 35 min | 1380 | 2 h | 568 |

Esterification time up to MW of about 750: 3 h 50 min
Distillate throughput: 242 g/h
The L(−)-lactide is worked up by known processes.
Total yield: 2000.4 g=69.4% of theory based on L(+)-lactic acid employed.

EXAMPLE 3

2 g of tin are dissolved in 606 g of Lactol 90. The solution is converted to polylactic acid by distillation off of water under about 0.02 bar and up to about 170° C. After 3.0 h, an average molecular weight of 834 has been reached. 360 g of distillate are then distilled off under about 0.01 bar and up to about 215° C. bottom temperature within 35 minutes. An additional 723 g of polylactic acid of average molecular weight 570 are fed to the distillation bottoms and converted to L(−)-lactide under the conditions given above. 711 g of distillate are obtained in 70 minutes.
Residue: 30 g
Distillate throughput: 612 g/h
The L(−)-lactide is worked up by known processes.

Total yield: 797.2 g=69.5% of theory based on L(+)-lactic acid employed.
The laboratory processes described in Examples 2 and 3 can readily be transferred to industrial scale.

EXAMPLE 4

3.4 g of tin dioctoate are added to 662 g of L(−)-polylactic acid of average molecular weight 1080, and 643 g of L(−)-lactide are distilled off at about 200° C. bottom temperature under a pressure of about 0.01 bar within 1.5 hours. Additional polylactic acid is fed to the distillation bottoms and converted in turn to L(−)-lactide under the conditions given above. This procedure is repeated several times:

| Additional polylactic acid fed in g | MW | L(−)-lactide distillation time | Distillate quantity g |
|---|---|---|---|
| 700 | 1080 | 1 h 12 min | 702 |
| 805 | 1080 | 1 h 25 min | 791 |

Residue: 20.0 g
Distillate throughput: 585 g/h
The L(−)-lactide is worked up by known processes.
Total yield: 1779 g=79.6% of theory based on L(+)-lactic acid employed.

What is claimed is:

1. A continuous or semicontinuous process for preparing L(−) or D(+)-lactide of substantial optical purity, wherein L(−) -polylactic acid is employed as the starting material to make L(−) lactide and D(+)-polylactic acid is employed as the starting material to make D(+)-lactide, wherein the starting materials are of 90% optical purity, and wherein the polylactic acid is heated to about 130 ° to 230° C., under reduced pressure, in the presence of about 0.05 to 1.0 per cent by weight of a catalyst selected from the group consisting of tin dust, tin halide and organic tin compounds derived from $C_1$–$C_{20}$ carboxylic acids.

2. The continuous or semicontinuous process of claim 1 wherein the organic tin compound is of the formula

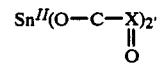

wherein X is a branched or unbranched alkyl, hydroxyalkyl or alkenyl radical having up to 19 carbon atoms or a naphthyl radical, or an organic tin compound of the formula

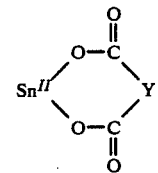

wherein Y is a branched or unbranched alkyl, hydroxyalkyl or alkenyl radical having up to 18 carbon atoms or a phenyl radical.

3. The continuous or semicontinuous process of claim 2, wherein the tin compound is selected from the group consisting of tin lactate, tin tantrate, tin oxalate, tin dicaprylate, tin dilaurate, tin dipalmitate, tin distearate, tin dioleate, tin α-naphthoate, tin β-naphthoate and tin dioctoate.

* * * * *